(12) United States Patent
Ma et al.

(10) Patent No.: US 12,226,095 B2
(45) Date of Patent: Feb. 18, 2025

(54) KNOTTER

(71) Applicant: BEIJING MED-ZENITH MEDICAL SCIENTIFIC CORPORATION LIMITED, Beijing (CN)

(72) Inventors: Zhiwei Ma, Beijing (CN); Danian Ke, Beijing (CN); Qingliang Zhou, Beijing (CN); Jian Meng, Beijing (CN)

(73) Assignee: BEIJING MED-ZENITH MEDICAL SCIENTIFIC CORPORATION LIMITED, Beijing (CN)

( * ) Notice: Subject to any disclaimer, the term of this patent is extended or adjusted under 35 U.S.C. 154(b) by 702 days.

(21) Appl. No.: 17/312,941

(22) PCT Filed: Dec. 9, 2019

(86) PCT No.: PCT/CN2019/124074
§ 371 (c)(1),
(2) Date: Jun. 11, 2021

(87) PCT Pub. No.: WO2020/119647
PCT Pub. Date: Jun. 18, 2020

(65) Prior Publication Data
US 2022/0047257 A1  Feb. 17, 2022

(30) Foreign Application Priority Data
Dec. 13, 2018 (CN) .......................... 201811526324.3

(51) Int. Cl.
*A61B 17/04* (2006.01)
(52) U.S. Cl.
CPC ...... *A61B 17/0469* (2013.01); *A61B 17/0467* (2013.01); *A61B 2017/047* (2013.01); *A61B 2017/0488* (2013.01)

(58) Field of Classification Search
CPC ............ A61B 17/0469; A61B 17/0467; A61B 17/0487; A61B 17/10; A61B 17/128;
(Continued)

(56) References Cited

U.S. PATENT DOCUMENTS

| 7,981,125 B1 | 7/2011 | Colvin et al. |
| 2016/0007986 A1 | 1/2016 | Sauer |

(Continued)

FOREIGN PATENT DOCUMENTS

| CN | 202892020 U | 4/2013 |
| CN | 204839666 U | 12/2015 |

(Continued)

OTHER PUBLICATIONS

International Search Report for corresponding application PCT/CN2019/124074 filed Dec. 9, 2019; Mail date Mar. 9, 2020.

*Primary Examiner* — Katherine M Rodjom
*Assistant Examiner* — Lindsey R. Rivers
(74) *Attorney, Agent, or Firm* — Samson G. Yu

(57) ABSTRACT

A knotter, including: a driving structure; a punching and shearing clip, a clip mouth of the punching and shearing clip having a first position in an open state, and a second position in a punching state when driven by the driving structure; and scissor having a first position in an open state when driven by the driving structure, and a second position in a shearing state when driven by the driving structure. The second position of the scissor is synchronized with the second position of the punching and shearing clip. The disclosure effectively solves the problem that the shearing knife of the knotter in the related art is unstable when cutting the suture line.

5 Claims, 4 Drawing Sheets

(58) Field of Classification Search
CPC ............ A61B 17/2804; A61B 17/3201; A61B 2017/047; A61B 2017/488
See application file for complete search history.

(56) References Cited

U.S. PATENT DOCUMENTS

| | | |
|---|---|---|
| 2018/0177503 A1 | 6/2018 | Miraki |
| 2018/0256159 A1 | 9/2018 | Sauer et al. |

FOREIGN PATENT DOCUMENTS

| | | | | |
|---|---|---|---|---|
| CN | 106037843 A | | 10/2016 | |
| CN | 106073836 A | * | 11/2016 | ......... A61B 17/0467 |
| CN | 205683123 U | | 11/2016 | |
| CN | 107007329 A | | 8/2017 | |
| CN | 210019475 U | | 2/2020 | |
| EP | 1832236 A2 | | 9/2007 | |
| JP | 3165292 B2 | | 2/1995 | |
| JP | H07108045 A | | 4/1995 | |
| WO | 9117712 A1 | | 11/1991 | |
| WO | WO-2016193280 A1 | * | 12/2016 | ............. A61B 17/29 |

\* cited by examiner

KNOTTER

TECHNICAL FIELD

The disclosure relates to the technical field of medical devices, and particularly to a knotter.

BACKGROUND

In recent years, with the development of surgical devices and cardiac surgical techniques, a minimally invasive surgery has become a hotspot direction in the development of various surgical disciplines. The minimally invasive surgery has the characteristics of small incision and fast recovery. Meanwhile, a surgeon is required to realize simple and fast postoperative suture and knotting operation in a minimally invasive surgery environment. There are two clinical knotting methods, which are manual knotting and device knotting.

A related surgical knotter generally enables a clamping element to plastically deform through a punching and shearing clip so as to clamp a suture line, and then the suture line is cut by a cutting knife or a shearing knife. This cutting mode has the defects that when cutting with the cutting knife, firstly, the cutting knife is required to have relatively high sharpness, cutting edges of a cutting knife made of a general material are easy to damage, secondly, the suture line is required to be in a tight state, and when a blade is delivered, a loose suture line is not easy to cut; and when the shearing knife is used, although the defect that the loose suture line is not easy to cut by the blade is improved, the requirement for the sharpness of the cutting edges is reduced, a handle of the shearing knife is unfolded by an elastic element to keep a knife head open, and then the handle is extruded by a driving rod to close the shearing knife and then cut the suture line. The elastic element is unstable in operation during use due to the space limitation.

SUMMARY

Some embodiments of the disclosure are to provide a knotter in order to solve the problem that a shearing knife of a knotter in the related art is unstable when cutting a suture line.

One embodiment of the disclosure provides a knotter, including: a driving structure, a punching and shearing clip and scissors. A clip mouth of the punching and shearing clip has a first position in an open state, and a second position in a punching state when driven by the driving structure. The scissors have a first position in an open state when driven by the driving structure, and a second position in a shearing state when driven by the driving structure. The second position of the scissors is synchronized with the second position of the punching and shearing clip.

In an embodiment, a first end of the scissors cooperates with the driving structure, and the cutting edges of the scissors are located at a second end of the scissors.

In an embodiment, the scissors include a first scissor arm and a second scissor arm, middle parts of the first scissor arm and the second scissor arm are connected by a pivot shaft, and the driving structure cooperates with a first end of the first scissor arm and a first end of the second scissor arm. When the first end of the first scissor arm is close to a second end of the second scissor arm, a second end of the first scissor arm is close to the second scissor arm; or the first end of the first scissor arm and the first end of the second scissor arm are connected and form the pivot shaft.

In an embodiment, the scissors are located at one side of the punching and shearing clip and are arranged adjacent to the punching and shearing clip.

In an embodiment, the driving structure includes a driving rod, and a first end of the driving rod cooperates with the punching and shearing clip and the scissors respectively.

In an embodiment, a first side part of the first end of the driving rod has scissor arm holes which cooperate with the scissors, and the first end of the scissors is located in the scissor arm holes.

In an embodiment, when the middle parts of the first scissor arm and the second scissor arm of the scissors have the pivot shaft, specific structures of the scissor arm holes include a first scissor arm hole and a second scissor arm hole, the first scissor arm of the scissors is located in the first scissor arm hole, and the second scissor arm of the scissors is located in the second scissor arm hole.

In an embodiment, a second side part of the first end of the driving rod has a punching and shearing clip abutting pressure plate which cooperates with the punching and shearing clip.

In an embodiment, the knotter further includes a handle and a sleeve, a first end of the sleeve is connected with the handle, the scissors and the punching and shearing clip are located at a second end of the sleeve, and the driving rod is located in the sleeve.

In an embodiment, the knotter further includes a drive portion, the drive portion is a manual drive portion arranged at the handle; or the drive portion is an automatic drive portion arranged at the handle.

By applying the technical solutions of the disclosure, when knotting the suture line, the driving structure of the knotter drives the punching and shearing clip to punch a clamping element, thereby knotting the suture line, and at the same time, the driving structure drives the scissors to be in the shearing state, so that the scissors may cut the knotted suture line. The scissors are in the open state and the shearing state when driven by the driving structure, and the structure is stable and reliable. The technical solutions of the disclosure effectively solve the problem that the shearing knife of the knotter in the related art is unstable when cutting the suture line.

BRIEF DESCRIPTION OF THE DRAWINGS

The drawings constituting a part of the disclosure are used for providing further understanding of the disclosure. Schematic embodiments of the disclosure and description thereof are used for illustrating the disclosure, rather than forming an improper limit to the disclosure. In the drawings.

Figure 1:
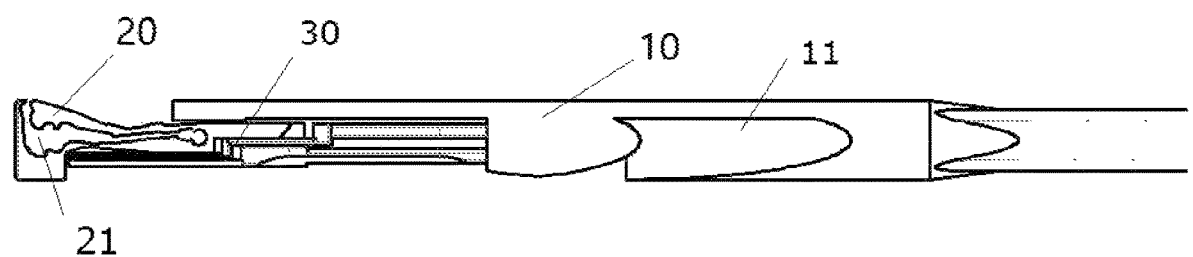
FIG. 1 is a partial structure diagram of an embodiment of a knotter according to the disclosure.

The above drawings include the following reference numbers:

10. driving structure; 11. scissor arm hole; 111. first scissor arm hole; 112. second scissor arm hole; 12. driving rod; 121. first side part; 122. second side part; 13. punching and shearing clip abutting pressure plate; 20. punching and shearing clip; 21. clip mouth; 30. scissors; 31. pivot shaft; 32. cutting edges; 33. first scissor arm; 331. first end of first scissor arm; 332. second end of first scissor arm; 34. second scissor arm; 341. first end of second scissor arm; 342. second end of second scissor arm; 40. sleeve; and 100. clamping element; 50. entrance hole; 51. outlet hole.

DETAILED DESCRIPTION OF THE EMBODIMENTS

It is to be noted that the embodiments of the disclosure and the characteristics in the embodiments can be combined under the condition of no conflicts. The disclosure is described below with reference to the drawings and the embodiments in detail.

As shown in FIG. 1 to FIG. 4, the knotter of the embodiments includes: a driving structure 10, a punching and shearing clip 20 and scissors 30. A clip mouth 21 of the punching and shearing clip 20 has a first position in an open state, and a second position in a punching state when driven by the driving structure 10. The scissors 30 have a first position in an open state when driven by the driving structure 10, and a second position in a shearing state when driven by the driving structure 10. The second position of the scissors 30 is synchronized with the second position of the punching and shearing clip 20.

Through disclosure of the technical solutions of the embodiment, when knotting a suture line, the driving structure 10 of the knotter drives the punching and shearing clip 20 to punch the clamping element 100, thereby knotting the suture line, and at the same time, the driving structure 10 drives the scissors 30 to be in the shearing state, so that the scissors 30 may cut the knotted suture line. The scissors 30 are in the open state and the shearing state when driven by the driving structure 10, and the structure is stable and reliable. The technical solution of the embodiment effectively solves the problem that the shearing knife of the knotter in the related art is unstable when cutting the suture line.

Figure 3:
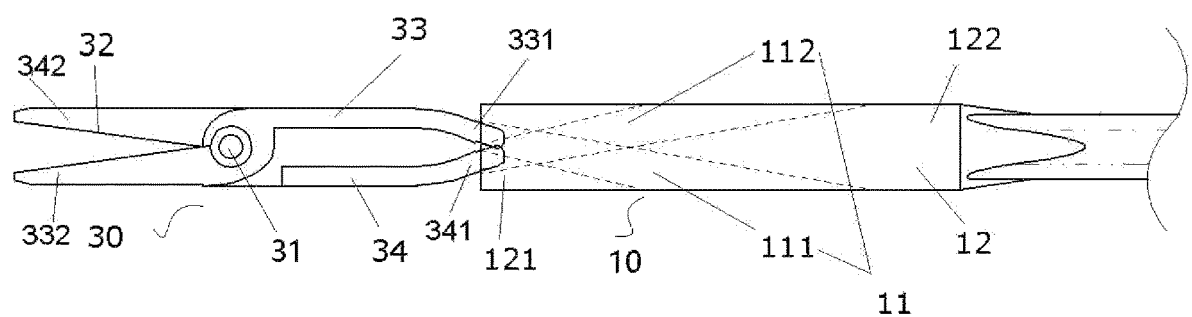
FIG. 3 is a structure diagram of scissor of the knotter of FIG. 1 in an open state.

As shown in FIG. 3, in the technical solution of the embodiment, a first end of the scissors 30 cooperates with the driving structure 10, and cutting edges 32 of the scissors 30 are located at a second end of the scissors 30. The scissors of the above structure are relatively low in processing cost and convenient to use. It is to be noted that the cutting edges 32 of the scissors 30 here are located at the second end of the scissors 30, the second end does not just indicate an end part and may indicate a partial area between the second end of the scissors 30 and the first end of the scissors 30, for example, the area from the pivot shaft 31 to the second end of the scissors 30 in FIG. 3 may be the cutting edges 32 entirely or may be the cutting edges 32 partially.

Figure 4:
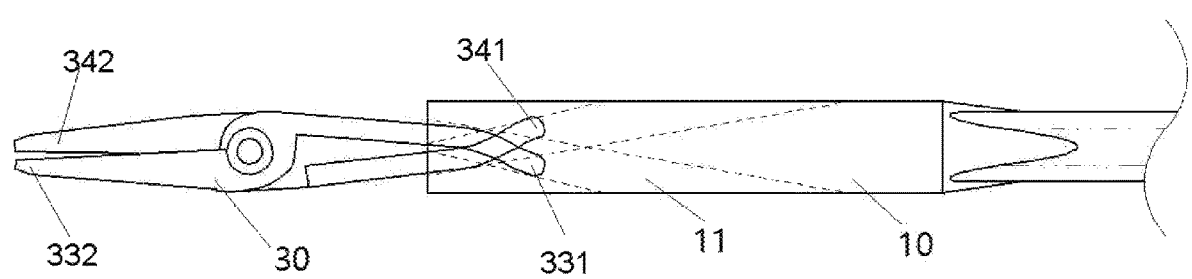
FIG. 4 is a structure diagram of the scissors of the knotter of FIG. 1 in a shearing state.

As shown in FIG. 3 and FIG. 4, in the technical solution of the embodiment, the scissors 30 include a first scissor arm 33 and a second scissor arm 34, middle parts of the first scissor arm 33 and the second scissor arm 34 are connected by a pivot shaft 31, and the driving structure 10 cooperates with a first end of the first scissor arm 33 and a first end of the second scissor arm 34. When the first end of the first scissor arm 33 is close to a second end of the second scissor arm 34, a second end of the first scissor arm 33 is close to the second scissor arm 34. The above structure is relatively low in processing cost, easy to mount and convenient to operate. Alternatively, the scissors 30 may be structured such that the first end of the first scissor arm 33 and the first end of the second scissor arm 34 are connected and form the pivot shaft 31.

Figure 2:
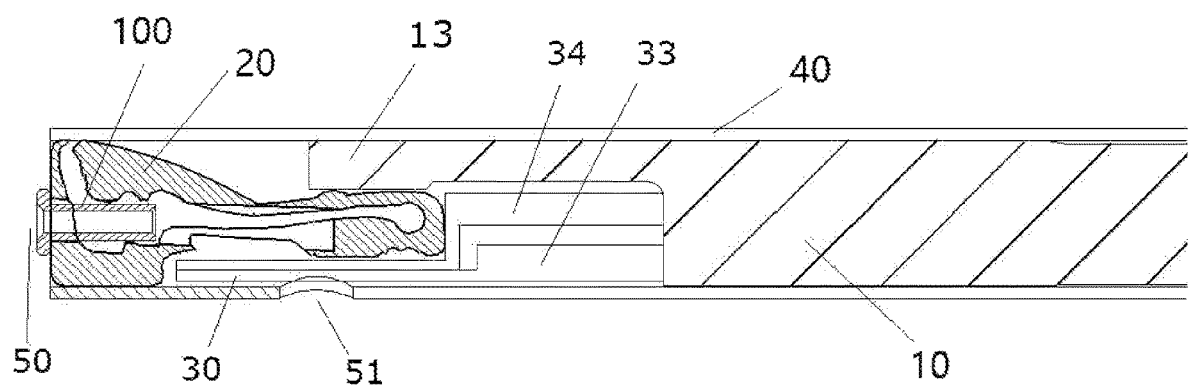
FIG. 2 is a partial cross-section diagram of the knotter of FIG. 1.

As shown in FIG. 1 and FIG. 2, in the technical solution of the embodiment, the scissors 30 are located at one side of the punching and shearing clip 20 and arranged adjacent to the punching and shearing clip 20. In this way, the distance between the scissors 30 and the punching and shearing clip 20 is relatively short, that is to say, the reserved length of the suture line is relatively short. After the suture line is clamped by a clamping element 100 and knotted, the suture line reserved from the clamping element 100 is the distance from the punching and shearing clip 20 to the scissors 30. Particularly, the punching and shearing clip 20 is located at a left side, and the scissors 30 are located at the right side of the punching and shearing clip 20.

As shown in FIG. 1 and FIG. 2, in the technical solution of the embodiment, the driving structure 10 includes a driving rod 12, and a first end of the driving rod 12 cooperates with both the punching and shearing clip 20 and the scissors 30. The above structure is relatively low in processing cost. The punching and shearing clip 20 includes two clip arms which are oppositely arranged, and a first end of the driving rod 12 enables the punching and shearing clip 20 to punch the clamping element 100 through punching and shearing clip arms, thereby knotting. Particularly, a first side part 121 of the first end of the driving rod 12 has scissor arm holes 11 which cooperate with the scissors 30, and the first end of the scissors 30 is located in the scissor arm holes 11. The above structure is compact, and punching and shearing can be completed through the same driving rod 12. When the middle parts of the first scissor arm 33 and the second scissor arm 34 of the scissors 30 have the pivot shaft, the scissor arm holes 11 include a first scissor arm hole 111 and a second scissor arm hole 112, a first scissor arm 33 of the scissors 30 is located in the first scissor arm hole 111, and a second scissor arm 34 of the scissors 30 is located in the second scissor arm hole 112. A second side of the driving rod 12 and a first side of the driving rod 12 are of a stepped structure, and the second side of the driving rod 12 is shorter than the first side of the driving rod 12. The driving rod 12 is a solid rod, the first scissor arm hole 111 and the second scissor arm hole 112 are respectively formed in oblique holes which cooperate with the first scissor arm 33 and the second scissor arm 34, and the first scissor arm hole 111 and the second scissor arm hole 112 are through holes which penetrate through a side wall of the driving rod 12 from the first end of the driving rod 12.

As shown in FIG. 2, in the technical solution of the embodiment, a second side part 122 of the first end of the driving rod 12 has a punching and shearing clip abutting pressure plate 13 which cooperates with the punching and shearing clip 20. The above structure is simple, and the knotting effect is good. Particularly, a bulged structure is arranged on an inner wall of the punching and shearing clip 20, in this way, the clamping element 100 is better in clamping effect, and the suture line is not easy to run out. The clamping element 100 is a clamping nail. The suture line enters through the entrance hole 50 on the left side of the clamping element 100. The suture line runs out of the sleeve 40 through the outlet hole 51.

As shown in FIG. 1 and FIG. 2, in the technical solution of the embodiment, the knotter further includes a handle and a sleeve 40, a first end of the sleeve 40 is connected with the handle, the scissors 30 and the punching and shearing clip 20 are located at a second end of the sleeve 40, and the driving rod 12 is located in the sleeve 40. The second end of the driving rod 12 is connected with the handle. The above structure is convenient to operate and is compact in structure. The sleeve 40 can stretch into a body, in this way, the suture line reserved in the body is relatively short.

In the technical solutions (not shown in figure) of the embodiments, the knotter further includes a drive portion, and the drive portion is a manual drive portion arranged at the handle. The above structure is relatively low in processing cost. The manual drive portion is a trigger structure. Certainly, the drive portion may also be an automatic drive portion arranged at the handle. In this way, the knotter may be automatically driven, and the labor intensity of an operator is reduced. The automatic drive portion includes a motor, a hydraulic structure and the like. By operating a switch button arranged on the knotter, the motor runs or the hydraulic structure drives. Alternatively, an electric push rod structure may also be applied. It is to be noted that after primary knotting is completed, the driving structure 10 resets under the action of an elastic member or other power element in the handle, so that the scissors 30 recover from the shearing state to the open state and get ready for secondary knotting and line shearing operation.

The above descriptions are only preferred embodiments of the disclosure and are not intended to limit the disclosure. Those skilled in the art should understand that the disclosure may have various changes and modifications. Any modification, equivalent substitution, improvement and the like made within the spirit and principle of the disclosure should be included in the protection scope of the disclosure.

What is claimed is:

1. A knotter, comprising:
    a driving structure;
    a punching and shearing clip, a clip mouth of the punching and shearing clip having a first position in an open state, and a second position in a punching state when driven by the driving structure; and
    scissors having a first position in an open state when driven by the driving structure, and a second position in a shearing state when driven by the driving structure;
    wherein the second position of the scissors is synchronized with the second position of the punching and shearing clip;
    a first end of the scissors cooperates with the driving structure, and cutting edges of the scissors being located at a second end of the scissors;
    the scissors comprise a first scissor arm and a second scissor arm,
    middle parts of the first scissor arm and the second scissor arm being connected by a pivot shaft, the driving structure cooperating with a first end of the first scissor arm and a first end of the second scissor arm, when the first end of the first scissor arm is close to a second end of the second scissor arm, a second end of the first scissor arm being close to the second scissor arm; the driving structure comprises a driving rod, a first end of the driving rod cooperating with the punching and shearing clip and the scissors respectively; a first side part of the first end of the driving rod has scissor arm holes which cooperate with the scissors, the first end of the scissors being located in the scissor arm holes, the scissor arm holes comprise a first scissor arm hole and a second scissor arm hole, the first scissor arm of the scissors being located in the first scissor arm hole, and the second scissor arm of the scissors being located in the second scissor arm hole,
    the first scissor arm hole and the second scissor arm hole are respectively formed in oblique holes which cooperate with the first scissor arm and the second scissor arm, an extension direction of the first scissor arm hole and an extension direction of the second scissor arm hole form an X shape.

2. The knotter as claimed in claim 1, wherein a second side part of the first end of the driving rod has a punching and shearing clip abutting pressure plate which cooperates with the punching and shearing clip.

3. The knotter as claimed in claim 1, wherein the knotter further comprises a handle and a sleeve, a first end of the sleeve being connected with the handle, the scissors and the punching and shearing clip being located at a second end of the sleeve, and the driving rod being located in the sleeve.

4. The knotter as claimed in claim 3, wherein the knotter further comprises a drive portion,
    the drive portion being a manual drive portion arranged at the handle; or
    the drive portion being an automatic drive portion arranged at the handle.

5. The knotter as claimed in claim 1, wherein the scissors are located at one side of the punching and shearing clip and are arranged adjacent to the punching and shearing clip.

* * * * *